United States Patent
Tanimoto et al.

(10) Patent No.: US 6,632,965 B1
(45) Date of Patent: Oct. 14, 2003

(54) PROCESS FOR PRODUCING ACROLEIN AND ACRYLIC ACID

(75) Inventors: Michio Tanimoto, Himeji (JP); Hiromi Yunoki, Himeji (JP); Hideyuki Hironaka, Himeji (JP); Naomasa Kimura, Okayama (JP)

(73) Assignee: Nippon Shokubai Co. Ltd., Osaka (JP)

( * ) Notice: Subject to any disclaimer, the term of this patent is extended or adjusted under 35 U.S.C. 154(b) by 564 days.

(21) Appl. No.: 09/633,292

(22) Filed: Aug. 4, 2000

(30) Foreign Application Priority Data

Aug. 4, 1999 (JP) .......................................... 11/221428

(51) Int. Cl.$^7$ .............................................. C07C 51/16
(52) U.S. Cl. ...................... 562/535; 562/545; 562/546; 562/547; 568/479; 568/480
(58) Field of Search .................................. 562/535, 545, 562/546, 547; 568/479, 480

(56) References Cited

U.S. PATENT DOCUMENTS 4,837,360 A * 6/1989 Kadowaki et al. .......... 562/546
5,276,178 A * 1/1994 Onedera et al. ............. 562/537

FOREIGN PATENT DOCUMENTS

EP  456837  6/1990

OTHER PUBLICATIONS

Japanese Patent Laid–Open No. 55–113730 (with English abstract) and corresponding USP 4,837,630.
Japanese Patent Publication No. 53–30688 (with English abstract) and corresponding USP 3,801,634.
Japanese Patent Laid–Open No. 3–215441 (with English abstract).
Japanese Patent Laid–Open No. 3–294238 (with English abstract).
Japanese Patent Laid Open No. 4–217932 (with English abstract) and corresponding USP 5,198,581.
Japanese Patent Laid–Open No. 6–321841 (with English abstract) and corresponding Canadian Patent Publication No. 2155973.
Japanese Patent Laid–Open No. 8–3093 (with English abstract).

* cited by examiner

*Primary Examiner*—Alan L. Rotman
*Assistant Examiner*—Hector M. Reyes
(74) *Attorney, Agent, or Firm*—Sherman & Shalloway

(57) ABSTRACT

The present invention provides a process for producing acrolein and acrylic acid by the vapor-phase oxidation of propylene in the presence of Mo—Bi—Fe-based compound oxide catalysts packed in a fixed-bed multitubular reactor wherein acrolein and acrylic acid can be stably produced in high yield for a long period of time. This process is characterized in that each reaction tube having two or more reaction zones disposed along the axis of the tube is packed with catalysts having different ratios of the Bi and/or Fe content to the Mo content in such a way that the ratio decreases from the gas inlet side toward the gas outlet side.

5 Claims, No Drawings

PROCESS FOR PRODUCING ACROLEIN AND ACRYLIC ACID

FIELD OF THE INVENTION

This invention relates to a process for producing acrolein and acrylic acid. More particularly, it relates to a process for producing acrolein and acrylic acid by the vapor-phase oxidation of propylene in the presence of a molybdenum-bismuth-iron-based oxide catalyst.

DESCRIPTION OF THE PRIOR ART

In producing acrolein and acrylic acid by the vapor-phase oxidation of propylene, a compound oxide catalyst containing molybdenum, bismuth and iron is usually used.

One disadvantage of this molybdenum-bismuth-iron-based compound oxide catalyst is that, when water vapor is present in the reaction system, the molybdenum component thereof tends to be sublimated and the sublimation of the molybdenum component is promoted especially at high temperatures. Moreover, in the case of exothermic reactions, such as the oxidation reaction of propylene, the catalyst bed tends to develop local areas having an abnormally high temperature (i.e., hot spots), which creates an environment in which the molybdenum component is more liable to sublimation. Furthermore, the sublimated molybdenum component tends to accumulate in areas having lower temperatures, leading to an increase in the pressure drop of the catalyst bed and hence a further rise in hot spot temperature.

In order to solve these problems, a variety of improvements in the molybdenum-bismuth-iron-based compound oxide catalyst or the process for producing acrolein and acrylic acid have been proposed. For example, Japanese Patent Laid-Open No. 113730/'80 discloses a process using two or more molybdenum-bismuth-iron-based compound oxide catalysts having different activities controlled by varying the content of an alkali metal (e.g., potassium or rubidium) wherein two or more axially disposed reaction zones of each reaction tube of a fixed-bed multitubular reactor are packed with the aforesaid catalysts in such a way that the activity increases from the gas inlet side of the reaction tube toward the gas outlet side thereof.

Problem to Be Solved by the Invention

In these conventional molybdenum-bismuth-iron-based compound oxide catalysts or processes for producing acrolein and acrylic acid, the problems have been solved to some extent. However, it is still desired to develop a more improved process for producing acrolein and acrylic acid with aid of a molybdenum-bismuth-iron-based compound oxide catalyst.

Accordingly, an object of the present invention is to provide a process for producing acrolein and acrylic acid by the vaporphase oxidation of propylene in the presence of molybdenum-bismuth-iron-based compound oxide catalysts wherein acrolein and acrylic acid can be stably produced in high yield for a long period of time.

Means for Solving the Problem

The above object of the present invention can be accomplished by a process for producing acrolein and acrylic acid by the vapor-phase catalytic oxidation of propylene with molecular oxygen or a molecular oxygen-containing gas in a fixed-bed multitubular reactor, which comprises (a) using, as the catalysts therefor, compound oxide catalysts of the general formula $$Mo_aW_bBi_cFe_dA_eB_fC_gD_hO_x \quad (I)$$

wherein Mo is molybdenum; W is tungsten, Bi is bismuth; Fe is iron; A is at least one element selected from the group consisting of cobalt and nickel; B is at least one element selected from the group consisting of phosphorus, antimony, boron, tin, cerium, niobium, lead, chromium and zinc; C is at least one element selected from the group consisting of alkali metals and thallium; D is at least one element selected from the group consisting of silicon, aluminum, titanium and zirconium; O is oxygen; a, b, c, d, e, f, g, h and x are the number of atoms of Mo, W, Bi, Fe, A, B, C, D and O, respectively; and when a is 12, b has a value of 0 to 5, c has a value of 0.1 to 10, d has a value of 0.1 to 10, e has a value of 1 to 20, f has a value of 0 to 5, g has a value of 0.001 to 3, h has a value of 0 to 30, and x has a value determined by the oxidation state of each element, and (b) packing the catalysts in each reaction tube having two or more reaction zones disposed along its axis in such a way that the catalyst packed in the reaction zone on the gas outlet side has a lower 20 ratio of the Bi and/or Fe content to the Mo content than the catalyst packed in the reaction zone on the gas inlet side.

Detailed Description of the Preferred Embodiments

The molybdenum-bismuth-iron-based compound oxide catalysts of the general formula (I) which are used in the present invention are well known per se and may be prepared according to well-known processes.

The essential feature of the present invention lies in the fact that each of the reaction tubes of a fixed-bed multitubular reactor is packed with molybdenum-bismuth-iron-based compound oxide catalysts in a specified manner. That is, according to the present invention, each reaction tube having two or more reaction zones (usually two or three reaction zones) disposed along the axis of the tube is packed with two or more catalysts having different ratios of the bismuth and/or iron content to the Mo content (hereinafter referred to as "bismuth-iron proportion") in such a way that the bismuth-iron proportion decreases from the gas inlet side toward the gas outlet side. For example, where each reaction tube has two reaction zones, two catalysts having different bismuth-iron proportions are prepared. Of these, the catalyst having a higher bismuth-iron proportion is packed in the reaction zone on the gas inlet side (hereinafter referred to as "the former-stage reaction zone"), and the catalyst having a lower bismuth-iron proportion is packed in the reaction zone on the gas outlet side (hereinafter referred to as "the latter-stage reaction zone").

When the contents of constituent elements are expressed as atomic ratios, the catalysts used in the present invention may contain 0.1 to 10 of Bi and 0.1 to 10 of Fe per 12 of molybdenum, as defined by the general formula (I). Accordingly, in the practice of the present invention, it is necessary to prepare two catalysts having different bismuth-iron proportions within these limits. Of these, the catalyst having a higher bismuth-iron proportion must be packed in the former-stage reaction zone, and the catalyst having a lower bismuth-iron proportion must be packed in the latter-stage reaction zone.

When the bismuth-iron proportion (ie., the atomic ratio of bismuth and/or iron to 12 of molybdenum) for the catalyst packed in the former-stage reaction one (hereinafter referred to as "the former-stage catalyst) is denoted by $M_1$, and the bismuth-iron proportion (i.e., the atomic ratio of bismuth and/or iron to 12 of molybdenum) for the catalyst packed in the latter-stage reaction zone (hereinafter referred to as "the latter-stage catalyst) is denoted by $M_2$, $M_1$ and $M_2$ preferably satisfy the relationship represented by $1<M_1/M_2\leq100$, more preferably $1.1\leq=M_1,M_2\leq20$, and most preferably $1.25\leq M_1/M_2\leq10$.

If $M_1$ is equal to or less than $M_2$ (i.e., $M_1/M_2\leq1$), it will be difficult to control the sublimation of the molybdenum component. On the other hand, if $M_1$ is excessively greater than $M_2$ (e.g., $100<M_1/M_2$), the process will be disadvantageous in that the desired catalyst performance cannot be achieved, the reaction temperature will be raised, and the sublimation of the molybdenum component will be promoted.

Accordingly, in a preferred embodiment of the present invention, it is desirable to prepare the former-stage catalyst and the latter-stage catalyst so as to satisfy the relationship represented by $1<M_1/M_2\leq100$, and pack them in the former-stage reaction zone and the latter-stage reaction zone, respectively.

In the present invention, no particular limitation is placed on the ratio of the group A element content to the Mo content (hereinafter referred to as "the proportion of the group A elements"). However, in a preferred embodiment of the present invention, two catalysts having different proportions of the group A elements are prepared and packed in the reaction zones in such a way that the proportion of the group A elements increases from the gas inlet side toward the gas outlet side. That is, two catalysts having different proportions of the group A elements are prepared so that the atomic ratio of the group A elements to 12 of molybdenum is in the range of 1 to 20. Then, the catalyst having a lower proportion of the group A elements is packed in the former-stage reaction zone, and the catalyst having a higher proportion of the group A elements is packed in the latter-stage reaction zone. More specifically, when the proportion of the group A elements (i.e., the atomic ratio of the group A elements to 12 of molybdenum) for the former-stage catalyst is denoted by $N_1$, and the proportion of the group A elements (i.e., the atomic ratio of the group A elements to 12 of molybdenum) for the latter-stage catalyst is denoted by $N_2$, $N_1$, and $N_2$ should preferably satisfy the relationship represented by $0.01\leq N_1/N_2<1$, more preferably $0.05\leq N_1/N_2<1$, and most preferably $0.1\leq N_{1/N2}<1$.

Accordingly, in a more preferred embodiment of the present invention, it is desirable to prepare the former-stage catalyst and the latter-stage catalyst so that they satisfy both of the relationships represented by $1<M_1/M_2<100$ and $0.01\leq N_1/N_2<1$, and pack them in the former-stage reaction zone and the latter-stage reaction zone, respectively.

Where each reaction tube has three reaction zones, the bismuth-iron proportions for the catalyst on the gas inlet side, the middle catalyst, and the catalyst on the gas outlet side are denoted by $M_1$, $M_2$ and $M_3$, respectively. Then, it is preferable that they satisfy both of the relationships represented by $1<M_1/M_2\leq100$ and $1<M_2/M_3\leq100$. Similarly, when the proportions of the group A elements for the catalyst on the gas inlet side, the middle catalyst, and the catalyst on the gas outlet side are denoted by $N_1$, $N_2$ and $N_3$, respectively, it is preferable that they satisfy both of the relationships represented by $0.01\leq N_1/N_2<1$ and $0.01\leq N_2/N_3<1$.

No particular limitation is placed on the shape and size of the catalysts used in the present invention, and any desired shape and size may be suitably chosen from well-known ones. For example, the catalysts may have any of various shapes such as balls, cylinders and rings.

No particular limitation is placed on the method for preparing the catalysts for use in the present invention. For example, shaped catalysts may be obtained by dissolving or dispersing required amounts of source compounds containing respective constituent elements suitably in an aqueous medium, heating the resulting solution or dispersion with stirring, evaporating it to dryness, pulverizing the resulting solid material to powder, shaping the powder into any desired shape according to a shaping technique such as extrusion molding or granulation shaping, and then firing the shaped pieces. During this shaping procedure, there may added materials which are generally known to be effective in improving the strength and structural integrity of catalysts, such as inorganic fibers (e.g., glass fibers) and various whiskers. Moreover, in order to control catalyst properties with good reproducibility, there may also be used additives generally known as powder binders, such as ammonium nitrate, cellulose, starch, polyvinyl alcohol and stearic acid.

The catalysts used in the present invention are not limited to the form of shaped catalysts as described above, but may also be in the form of supported catalysts. Supported catalysts may be obtained by depositing a source compound on a carrier generally known as an inert carrier, such as alumina, silica, silica-alumina, silicon carbide, titanium oxide, magnesium oxide, sponge aluminum or silica-titania, and then firing the resulting supported pieces. Also in the case of supported catalysts, the above-described materials such as inorganic fibers and whiskers may be used to improve the strength and structural integrity of the catalysts. Moreover, the above-described powder binders such as ammonium nitrate may also be used to control catalyst properties with good reproducibility.

In preparing the catalysts for use in the present invention, the firing of the precursor such as shaped pieces or supported pieces may be carried out, for example, by heating the shaped pieces or loaded carrier in a stream of air at a temperature of 300 to 600° C. for a period of about 1 to 10 hours.

No particular limitation is placed on the reaction conditions employed for the oxidation reaction of the present invention. There may be employed any reaction conditions commonly known to be useful in a process for producing acrolein and acrylic acid by the vapor-phase catalytic oxidation of propylene in a fixed-bed multitubular reactor. For example, the oxidation reaction of the present invention may be carried out by providing a gaseous mixture composed of 1 to 15% by volume of propylene, 3 to 30% by volume of molecular oxygen, 0 to 60% by volume of water vapor, and 20 to 80% by volume of an inert gas comprising nitrogen, carbon dioxide and the like, and passing this gaseous mixture through the reaction zones of the reaction tubes packed with the catalysts at a temperature of 250 to 450° C., a pressure of 0.1 to 1 MPa, and a space velocity (SV) of 300 to 5,000 $hr^{-1}$.

Effects of the Invention

The process of the present invention makes it possible to suppress the sublimation of the molybdenum component of the catalysts effectively and thereby maintain the catalyst performance stably for a long period of time. Consequently, the production of acrolein and acrylic acid from propylene can be stably continued in high yield for a long period of time. Moreover, the process of the present invention makes it possible to suppress the accumulation of sublimated molybdenum component and, in turn, an increase in the pressure drop of the catalyst bed, and thereby reduce utility costs such as electric power costs for the compressor.

EXAMPLES

The present invention is more specifically explained with reference to the following examples. The conversion of propylene, selectivity, yield and ΔP (kPa) are defined as follows.

Conversion of propylene (mole %)=(Number of moles of propylene reacted)/(Number of moles of propylene fed)×100

Selectivity (mole %)=(Number of moles of acrolein and acrylic acid formed)/(Number of moles of propylene reacted)×100

Yield (mole %)=(Number of moles of acrolein and acrylic acid formed)/(Number of moles of propylene fed)×100

ΔP (kPa)=(Inlet pressure of reactor)—(Outlet pressure of reactor)

Example 1
[Preparation of Catalysts]

While 3,000 ml of water was being heated with stirring, 1,000 g of ammonium paramolybdate and 26 g of ammonium paratungstate were dissolved therein. Separately, 687 g of cobalt nitrate and 191 g of ferric nitrate were dissolved in 1,000 ml of water. Moreover, 275 g of bismuth nitrate was dissolved in an aqueous nitric acid solution composed of 50 g of concentrated nitric acid and 200 g of water. The foregoing three aqueous solutions were mixed by adding the second and third aqueous solutions dropwise to the first aqueous solution. Then, an aqueous solution prepared by dissolving 2.4 g of potassium nitrate in 50 ml of water, and 142 g of a silica sol having a concentration of 20% by weight were successively added to and mixed with the above mixed aqueous solution.

The suspension thus obtained was heated with stirring, evaporated to dryness, and dried. After the resulting solid material was pulverized to powder, this powder was shaped into cylinders having a diameter of 6 mm and a length of 6.6 mm, and fired in a stream of air at 460° C. for 8 hours to obtain the catalyst (1). The composition (i.e., the atomic ratio of the constituent elements except oxygen; the same shall apply hereinafter) of this catalyst (1) was as follows.

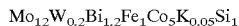
$Mo_{12}W_{0.2}Bi_{1.2}Fe_1Co_5K_{0.05}Si_1$

In the catalyst (1), the bismuth-iron proportion is 2.2/12, and the proportion of the group A elements is 5/12.

Next, the catalyst (2) was prepared according to the same procedure as described above for the preparation of the catalyst (1), except that the amount of bismuth nitrate was changed to 572 g, and the amount of ferric nitrate was changed to 381 g. The composition of this catalyst (2) was as follows.

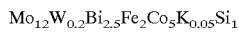
$Mo_{12}W_{0.2}Bi_{2.5}Fe_2Co_5K_{0.05}Si_1$

In the catalyst (2), the bismuth-iron proportion is 4.5/12, and the proportion of the group A elements is 5/12.
[Oxidation Reaction]

A stainless steel tubular reactor having a diameter of 25 mm was packed with 500 ml of the catalyst (2) on the gas inlet side and 1,000 ml of the catalyst (1) on the gas outlet side. Then, a gaseous mixture composed of 8% by volume of propylene, 14% by volume of oxygen, 10% by volume of water vapor, and 68% by volume of an inert gas comprising nitrogen and the like was introduced through the inlet of the aforesaid tubular reactor at a contact time of 2.4 seconds, and the reaction was continued for 8,000 hours. The performance at the initial stage of the reaction and the performance after the lapse of 8,000 hours are shown in Table 1.

Comparative Example 1

Reaction was carried out in the same manner as in Example 1, except that 1,500 ml of the catalyst (1) alone was used. The results thus obtained are shown in Table 1.

Comparative Example 2

Reaction was carried out in the same manner as in Example 1, except that 1,500 ml of the catalyst (2) alone was used. The results thus obtained are shown in Table 1.

TABLE 1

| | | Reaction time (hrs.) | Reaction temperature (° C.) | Conversion (mole %) | Selectivity (mole %) | Yield (mole %) | ΔP (kPa) |
|---|---|---|---|---|---|---|---|
| Example 1 | Initial stage | | 310 | 98.4 | 94.7 | 93.2 | 20.0 |
| | | 8,000 | 325 | 98.2 | 94.9 | 93.2 | 22.0 |
| Comparative Example 1 | Initial stage | | 300 | 98.5 | 92.2 | 90.8 | 19.5 |
| | | 8,000 | 315 | 98.4 | 90.4 | 89.0 | 30.0 |
| Comparative Example 2 | Initial stage | | 310 | 79.7 | 95.8 | 76.4 | 21.0 |
| | | 8,000 | 325 | 81.0 | 95.6 | 77.4 | 21.5 |

Example 2
[Preparation of Catalysts]

While 3,000 ml of water was being heated with stirring, 1,000 g of ammonium paramolybdate and 26 g of ammonium paratungstate were dissolved therein. Separately, 481 g of cobalt nitrate, 480 g of nickel nitrate, and 286 g of ferric nitrate were dissolved in 1,000 ml of water. Moreover, 412 g of bismuth nitrate was dissolved in an aqueous nitric acid solution composed of 50 g of concentrated nitric acid and 200 g of water. The foregoing three aqueous solutions were mixed by adding the second and third aqueous solutions dropwise to the first aqueous solution. Then, an aqueous solution prepared by dissolving 3.8 g of potassium nitrate in 50 ml of water, and 142 g of a silica sol having a concentration of 20% by weight were successively added to and mixed with the above mixed aqueous solution.

The suspension thus obtained was heated with stirring, evaporated to dryness, and dried. After the resulting solid material was pulverized to powder, this powder was shaped into rings having an outer diameter of 6 mm, an inner diameter of 2 mm, and a length of 6.6 mm, and fired in a stream of air at 480° C. for 8 hours to obtain the catalyst (3). The composition of this catalyst (3) was as follows.

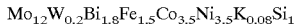
$Mo_{12}W_{0.2}Bi_{1.8}Fe_{1.5}Co_{3.5}Ni_{3.5}K_{0.08}Si_1$

In the catalyst (3), the bismuth-iron proportion is 3.3/12, and the proportion of the group A elements is 7/12.

Next, the catalyst (4) was prepared according to the same procedure as described above for the preparation of the catalyst (3), except that the amount of cobalt nitrate was changed to 343 g, the amount of bismuth nitrate was changed to 687 g, and the amount of nickel nitrate was changed to 343 g. The composition of this catalyst (4) was as follows.

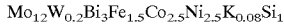
$Mo_{12}W_{0.2}Bi_3Fe_{1.5}Co_{2.5}Ni_{2.5}K_{0.08}Si_1$

In the catalyst (4), the bismuth-iron proportion is 4.5/12, and the proportion of the group A elements is 5/12.

[Oxidation Reaction]

Reaction was carried out in the same manner as in Example 1, except that the catalyst (4) was used in place of the catalyst (2), and the catalyst (3) was used in place of the catalyst (1). The results thus obtained are shown in Table 2.

Comparative Example 3

Reaction was carried out in the same manner as in Example 2, except that 1,500 ml of the catalyst (3) alone was used. The results thus obtained are shown in Table 2.

Comparative Example 4

Reaction was carried out in the same manner as in Example 2, except that 1,500 ml of the catalyst (4) alone was used. The results thus obtained are shown in Table 2.

TABLE 2

|  | Reaction time (hrs.) | Reaction temperature (° C.) | Conversion (mole %) | Selectivity (mole %) | Yield (mole %) | ΔP (kPa) |
|---|---|---|---|---|---|---|
| Example 2 | Initial stage | 310 | 98.3 | 95.3 | 93.7 | 16.7 |
|  | 8,000 | 320 | 98.2 | 95.2 | 93.5 | 17.5 |
| Comparative Example 3 | Initial stage | 300 | 98.7 | 92.5 | 91.3 | 16.9 |
|  | 8,000 | 310 | 98.8 | 90.8 | 89.7 | 23.7 |
| Comparative Example 4 | Initial stage | 310 | 80.1 | 96.0 | 76.9 | 16.2 |
|  | 8,000 | 320 | 77.4 | 96.3 | 74.5 | 16.4 |

Example 3

[Preparation of Catalysts]

While 3,000 ml of water was being heated with stirring, 1,000 g of ammonium paramolybdate and 26 g of ammonium paratungstate were dissolved therein. Separately, 756 g of cobalt nitrate, 412 g of nickel nitrate, and 191 g of ferric nitrate were dissolved in 1,000 ml of water. Moreover, 229 g of bismuth nitrate was dissolved in an aqueous nitric acid solution composed of 50 g of concentrated nitric acid and 200 g of water. The foregoing three aqueous solutions were mixed by adding the second and third aqueous solutions dropwise to the first aqueous solution. Then, an aqueous solution prepared by dissolving 1.8 g of cesium nitrate in 50 ml of water, and 142 g of a silica sol having a concentration of 20% by weight were successively added to and mixed with the above mixed aqueous solution.

The suspension thus obtained was heated with stirring, evaporated to dryness, and dried. After the resulting solid material was pulverized to powder, this powder was shaped into rings having an outer diameter of 6 mm, an inner diameter of 2 mm, and a length of 6.6 mm, and fired in a stream of air at 480° C. for 8 hours to obtain the catalyst (5). The composition of this catalyst (5) was as follows.

$$Mo_{12}W_{0.2}Bi_1Fe_1Co_{5.5}Ni_3Cs_{0.02}Si_1$$

In the catalyst (5), the bismuth-iron proportion is 2/12, and the proportion of the group A elements is 8.5/12.

Next, the catalyst (6) was prepared according to the same procedure as described above for the preparation of the catalyst (5), except that the amount of bismuth nitrate was changed to 572 g, the amount of ferric nitrate was changed to 381 g, the amount of nickel nitrate was changed to 137 g, and the amount of cobalt nitrate was changed to 550 g. The composition of this catalyst (6) was as follows.

$$Mo_{12}W_{0.2}Bi_{2.5}Fe_2Co_4Ni_1Cs_{0.02}Si_1$$

In the catalyst (6), the bismuth-iron proportion is 4.5/12, and the proportion of the group A elements is 5/12.

Furthermore, the catalyst (7) was prepared according to the same procedure as described above for the preparation of the catalyst (6), except that the amount of bismuth nitrate was changed to 801 g, the amount of ferric nitrate was changed to 572 g, the amount of nickel nitrate was changed to 0 g, and the amount of cobalt nitrate was changed to 343 g. The composition of this catalyst (7) was as follows.

$$Mo_{12}W_{0.2}Bi_{3.5}Fe_3Co_{2.5}Cs_{0.02}Si_1$$

In the catalyst (7), the bismuth-iron proportion is 6.5/12, and the proportion of the group A elements is 2.5/12.

[Oxidation Reaction]

A stainless steel tubular reactor having a diameter of 25 mm was packed with 500 ml of the catalyst (7), 500 ml of the catalyst (6), and 500 ml of the catalyst (5) in such a way that they were arranged in that order from the gas inlet side toward the gas outlet side. Then, a gaseous mixture composed of 10% by volume of propylene, 16% by volume of oxygen, 10% by volume of water vapor, and 64% by volume of an inert gas comprising nitrogen and the like was introduced through the inlet of the aforesaid tubular reactor at a contact time of 2.4 seconds, and the reaction was continued for 8,000 hours. The performance at the initial stage of the reaction and the performance after the lapse of 8,000 hours are shown in Table 3.

Comparative Example 5

Reaction was carried out in the same manner as in Example 3, except that 1,500 ml of the catalyst (5) alone was used. The results thus obtained are shown in Table 3.

Comparative Example 6

Reaction was carried out in the same manner as in Example 3, except that 1,500 ml of the catalyst (6) alone was used. The results thus obtained are shown in Table 3.

Comparative Example 7

Reaction was carried out in the same manner as in Example 3, except that 1,500 ml of the catalyst (7) alone was used. The results thus obtained are shown in Table 3.

TABLE 3

|  | Reaction time (hrs.) | Reaction temperature (° C.) | Conversion (mole %) | Selectivity (mole %) | Yield (mole %) | ΔP (kPa) |
|---|---|---|---|---|---|---|
| Example 3 | Initial stage | 310 | 98.1 | 94.3 | 92.5 | 17.3 |
|  | 8,000 | 320 | 97.9 | 94.4 | 92.4 | 19.7 |
| Comparative Example 5 | Initial stage | The recitation could not be continued because of a marked in hot spot temperature | | | | |
| Comparative Example 6 | Initial stage | 310 | 82.4 | 94.6 | 78.0 | 17.0 |
|  | 8,000 | 320 | 80.4 | 95.3 | 76.6 | 17.8 |
| Comparative Example 7 | Initial stage | 310 | 70.3 | 95.6 | 67.2 | 17.3 |
|  | 8,000 | 320 | 68.7 | 95.7 | 65.7 | 17.5 |

Example 4

Reaction was carried out in the same manner as in Example 1, except that the catalyst (3) was used in place of the catalyst (1). The results thus obtained are shown in Table 4.

Example 5

Reaction was carried out in the same manner as in Example 1, except that the catalyst (6) was used in place of the catalyst (2). The results thus obtained are shown in Table 4.

TABLE 4

|  |  | Reaction time (hrs.) | Reaction temperature (° C.) | Conversion (mole %) | Selectivity (mole %) | Yield (mole %) | ΔP (kPa) |
|---|---|---|---|---|---|---|---|
| Example 4 | | Initial stage | 310 | 98.1 | 94.7 | 92.9 | 17.7 |
| | | 8,000 | 321 | 98.3 | 94.4 | 92.8 | 19.2 |
| Example 5 | | Initial stage | 310 | 98.0 | 94.6 | 92.7 | 18.9 |
| | | 8,000 | 325 | 98.1 | 94.2 | 92.4 | 20.8 |

What is claimed is:

1. A process for producing acrolein and acrylic acid by the vapor-phase catalytic oxidation of propylene with molecular oxygen or a molecular oxygen-containing gas in a fixed-bed multitubular reactor, which comprises (a) using, as the catalysts therefor, compound oxide catalysts of the formula $$Mo_{12}W_bBi_cFe_dA_eB_fC_gD_hO_x \qquad (I)$$

wherein Mo is molybdenum; W is tungsten, Bi is bismuth; Fe is iron; A is at least one element selected from the group consisting of cobalt and nickel; B is at least one element selected from the group consisting of phosphorus, antimony, boron, tin, cerium, niobium, lead, chromium and zinc; C is at least one element selected from the group consisting of alkali metals and thallium; D is at least one element selected from the group consisting of silicon, aluminum, titanium and zirconium; O is oxygen; b, c, d, e, f, g, h and x are the number of atoms of W, Bi, Fe, A, B, C, D and O, respectively; and b has a value of 0 to 5, c has a value of 0.1 to 10, d has a value of 0.1 to 10, e has a value of 1 to 20, f has a value of 0 to 5, g has a value of 0.001 to 3, h has a value of 0 to 30, and x has a value determined by the oxidation state of each element, and (b) packing said catalysts in each reaction tube having two or more reaction zones disposed along the axis of the tube in such a way that the catalyst packed in the reaction zone on the gas outlet side has a lower ratio of the Bi and Fe content to the Mo content than the catalyst packed in the reaction zone on the gas inlet side.

2. A process as claim in claim 1 wherein, when the ratio of the Bi and Fe content to the Mo content for the catalyst packed in the reaction zone on the gas inlet side is denoted by $M_1$, and the ratio of the Bi and Fe content to the Mo content for the catalyst packed in the reaction zone on the gas outlet side is denoted by $M_2$, $M_1$ and $M_2$ satisfy the relationship represented by $1<M_1/M_2<100$.

3. A process as claim in claim 1 or 2 wherein catalysts having different ratios of the group A element content to the Mo content are packed in the reaction zones in such a way that the ratio increases from the gas inlet side toward the gas outlet side.

4. A process as claim in claim 3 wherein, when the ratio of the group A element content to the Mo content for the catalyst packed in the reaction zone on the gas inlet side is denoted by $N_1$, and the ratio of the group A element content to the Mo content for the catalyst packed in the reaction zone on the gas outlet side is denoted by $N_2$, $N_1$ and $N_2$ satisfy the relationship represented by $0.01 \leq N_1/N_2 < 1$.

5. A process as claim in any of claims 1 to 4 wherein, when the number of the reaction zones is 2 or 3.

* * * * *